US00PP27094P2

(12) United States Plant Patent
Hartman

(10) Patent No.: US PP27,094 P2
(45) Date of Patent: Aug. 23, 2016

(54) ***CALADIUM* PLANT NAMED 'CHINOOK'**

(50) Latin Name: *Caladium×hortulanum*
Varietal Denomination: Chinook

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 90 days.

(21) Appl. No.: 14/544,173

(22) Filed: Dec. 4, 2014

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Chinook', characterized by its compact, upright and uniformly mounding plant habit; vigorous growth habit and very rapid growth rate; lance-type leaves that are medium green in color flushed with salmon pink and dark pink-colored venation; and good landscape performance.

4 Drawing Sheets

Botanical designation: *Caladium×hortulanum.*
Cultivar denomination: 'CHINOOK'.

BACKGROUND OF THE INVENTION

The present invention relates to a new and distinct cultivar of *Caladium* plant, botanically known as *Caladium×hortulanum*, commercially referred to as a lance leaf-type *Caladium* and hereinafter referred to by the name 'Chinook'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2008 in Avon Park, Fla. of *Caladium×hortulanum* 'White Wonder', disclosed in U.S. Plant Pat. No. 21,044, as the female, or seed, parent with *Caladium×hortulanum* 'Kathleen', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2009.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since March, 2010 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Chinook'. These characteristics in combination distinguish 'Chinook' as a new and distinct *Caladium* plant:

1. Compact, upright and uniformly mounding plant habit.
2. Vigorous growth habit and very rapid growth rate.
3. Lance-type leaves that are medium green in color flushed with salmon pink and dark pink-colored venation.
4. Good landscape performance.

Plants of the new *Caladium* differ primarily from plants of the female parent, 'White Wonder', in the following characteristics:

1. Plants of the new *Caladium* are more mounding than and not as upright as plants of 'White Wonder'.
2. Plants of the new *Caladium* are faster growing and produce finished plants about two to three weeks earlier than plants of 'White Wonder'.
3. Plants of the new *Caladium* and 'White Wonder' differ in leaf color as leaves of plants of 'White Wonder' are white to light pink in color with light pink to white-colored venation and dark green-colored margins.

Plants of the new *Caladium* differ primarily from plants of the male parent, 'Kathleen', in the following characteristics:

1. Plants of the new *Caladium* are more compact than plants of 'Kathleen'.
2. Plants of the new *Caladium* are more mounding than and not as upright as plants of 'Kathleen'.
3. Plants of the new *Caladium* and 'Kathleen' differ in leaf shape and color as leaves of plants of 'Kathleen' are fancy-types and medium green in color with salmon pink-colored centers and light pink-colored venation.

Plants of the new *Caladium* can be compared to plants of *Caladium×hortulanum* 'Florida Sweetheart', disclosed in U.S. Plant Pat. No. 8,526. In side-by-side comparisons, plants of the new *Caladium* differed primarily from plants of 'Florida Sweetheart' in the following characteristics:

1. Plants of the new *Caladium* were faster growing and produce finished plants about one week earlier than plants of 'Florida Sweetheart'.

2. Plants of the new *Caladium* and 'Florida Sweetheart' differed in leaf shape and color as leaves of plants of 'Florida Sweetheart' were broadly ovate in shape and pink in color with medium green to white-colored margins.

Plants of the new *Caladium* can also be compared to plants of *Caladium×hortulanum* 'Blushing Bride', disclosed in U.S. Plant Pat. No. 22,213. In side-by-side comparisons, plants of the new *Caladium* differed primarily from plants of 'Blushing Bride' in the following characteristics:

1. Plants of the new *Caladium* were faster growing and produce finished plants about one week earlier than plants of 'Blushing Bride'.
2. Plants of the new *Caladium* and 'Blushing Bride' differed in leaf color as leaves of plants of 'Blushing Bride' were pink in color with narrow medium green-colored margins.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Chinook' in a container and grown in a shadehouse (tuber not de-eyed).

The photograph at the top of the second sheet is a comparison view of typical potted plants of the female parent, 'White Wonder' (left), 'Chinook' (center) and the male parent, 'Kathleen' (right).

The photograph at the bottom of the second sheet is a comparison view of typical potted plants of 'Florida Sweetheart' (left), 'Chinook' (center) and 'Blushing Bride' (right).

The photograph at the top of the third sheet is a comparison view of typical plants of 'Chinook' grown in containers; the plant on the right has not had its tuber de-eyed and the plant on the left has had its tuber de-eyed prior to planting.

The photograph at the bottom of the third sheet is a side perspective view of typical plants of 'Chinook' grown in an open field.

The photograph at the top of the fourth sheet is a close-up view of typical freshly-harvested tubers and roots of 'Chinook' plants.

The photograph at the bottom of the fourth sheet is a close-up view of typical inflorescences of 'Chinook'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were four weeks old, and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Chinook'.

Parentage:

*Female, or seed, parent.*—*Caladium×hortulanum* 'White Wonder', disclosed in U.S. Plant Pat. No. 21,044.

*Male, or pollen, parent.*—*Caladium×hortulanum* 'Kathleen', not patented.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented and somewhat flattened; individual segments elliptic to ovate in shape. Height: About 3.2 cm. Diameter: About 5.3 cm to 6 cm. Segment height: About 2.2 cm. Segment diameter: About 2.6 cm. Texture: Thick, starchy; somewhat brittle. Color: Epidermis, freshly-harvested: Close to 199A to 199B. Epidermis, dried: Close to 200A. Cortical tissue: Close to 155A and 150D. Axillary buds: Close to 27A. Root description: Thick, fleshy contractile roots; color, close to 155C and 199C. Rooting habit: Sparse to medium density.

Plant description:

*Plant type*.—Herbaceous perennial; suitable as a potted plant in containers 15-cm to 25-cm and suitable as a landscape plant in shaded areas.

*Plant and growth habit*.—Compact, upright and uniformly mounded plant habit; vigorous and dense growth habit; very rapid growth rate, potted plants in finished or saleable form in about four weeks after planting tubers; leaf petioles and leaves arise from one or more growing points on tubers; petioles mostly upright and leaning outwardly with development.

*Plant height, from soil level to top of foliar plane, shadehouse-grown potted plants*.—About 20 cm to 25 cm.

*Plant height, from soil level to top of inflorescences, shadehouse-grown potted plants*.—About 31.2 cm.

*Plant diameter or spread, shadehouse-grown potted plants*.—About 38 cm to 42 cm.

*Number of shoots per plant, shadehouse-grown potted plants, tubers not de-eyed*.—About three develop per #1 tuber.

*Number of shoots per plant, shadehouse-grown potted plants, tubers de-eyed*.—About three to four develop per #1 tuber.

*Cataphylls, shadehouse-grown potted plants*.—Length: About 3.5 cm to 4.8 cm. Width: About 1 cm to 1.4 cm. Shape: Wedge-shaped. Apex: Acuminate or emarginate. Base: Sheathing the stem. Color, inner surface: Close to N155C; colors and patterns of the outside surface are visible on the inner surface. Color, outer surface: Close to 199C tinged with close to 147C, streaked and stippled with close to 147A tinged with close to N200A; with development, color becoming closer to 199A.

Leaf description:

*Arrangement and type*.—Alternate; simple; lance-type.

*Length, shadehouse-grown potted plants*.—About 16.5 cm to 20 cm.

*Width, shadehouse-grown potted plants, flattened*.—About 9.7 cm to 12.5 cm.

*Shape*.—Ovate to lanceolate.

*Apex*.—Acuminate to acute.

*Base*.—Sagittate to peltate.

*Margin*.—Entire; undulate with broad undulations.

*Texture, upper and lower surfaces*.—Smooth, glabrous.

*Luster, upper surface*.—Dull sheen.

*Luster, lower surface*.—Glaucous, dull sheen.

*Venation pattern*.—Pinnate.

*Color, shadehouse-grown potted plants*.—Developing and fully expanded leaves, upper surface: Main color and towards margin: Close to 147B with random flecking, close to 194C. Interveinal panels: Mottled and flecking, close to 195B, 147A to 147B and 177B. Margin edge: Close to 187B. Basal notch: Close to 187B. Midrib and primary venation: Close to 53C and 53B to 53C with streaks, close to 49C to 49D; areas surrounding venation, close to 50C and 50B to 50C. Developing and fully expanded leaves, lower surface: Main color and towards margin: Close to 191A and 148B. Interveinal panels: Towards the margins, close to 148C with flecking, close to 49D; central, close to 51C mottled with close to 49D and 195B. Margin edge: Close to 187B. Basal notch: Close to 187B. Midrib and primary venation: Close to 195B to 195B streaked with close to 49D.

*Petioles*.—Aspect: Initially upright and straight; with development, leaning outwardly; flexible. Length, shadehouse-grown potted plants: About 17 cm to 19 cm. Diameter, distal, shadehouse-grown potted plants: About 3 mm to 3.5 mm. Diameter, proximal, shadehouse-grown potted plants: About 5 mm to 7.5 mm. Texture: Smooth, glabrous; glaucous. Color, shadehouse-grown potted plants, Just below the leaf and petiole junction: Close to 199D tinged with close to 182D and 147C, stippled, streaked and striped with close to 147A tinged with close to 200C. Overall: Close to 199D tinged with close to 182D and 147C, stippled, streaked and striped with close to 147A tinged with close to 200C; occasionally flushed with close to 182C to 182D. Wing length, shadehouse-grown potted plants: About 3.5 cm to 5 cm. Wing diameter, shadehouse-grown potted plants: About 7 mm. Texture, inner and outer surfaces: Smooth, glabrous. Wing color, shadehouse-grown potted plants, inner surface: Close to N155C. Wing color, shadehouse-grown potted plants, outer surface: Close to 199D tinged with close to 182D and 147C and stippled, streaked and striped with close to 147A tinged with close to 200C.

Inflorescence description: Inflorescences observed on four week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring in central Florida; early flowering habit, flowers develop about four weeks after growth commences; inflorescences last about three days before fading; inflorescences persistent.

*Spathe*.—Length, overall: About 10 cm. Length, distal open portion: About 6.5 cm. Length, proximal closed portion: About 3.5 cm. Width, distal open portion: About 4.8 cm. Width, at constriction: About 1.2 cm. Width, proximal closed portion: About 2.7 cm. Shape: Elliptic. Apex: Acute to acuminate; forward pointing. Base: Obtuse. Margin: Entire. Texture, front and rear surfaces: Smooth, glabrous. Luster, front surface: Dull sheen. Luster, rear surface: Glaucous. Color, front surface: Distal open portion: Close to 155A tinged with close to 145D; with development, color becoming closer to 199C to 199D. Proximal closed portion: Close to 194A and 194B; towards the base, darkly flushed with close to N186D and 187C; color does not change with development. Color, rear surface: Distal open portion: Close to 155A and 155C flushed with close to 150D and 145D; towards the center, tinged with close to 147D; color does not change with development. Proximal closed portion: Close to 147B and 146C occasionally mottled and flecked with close to 147D tinged with close to 182D; color does not change with development.

*Spadix*.—Length: About 7.5 cm. Length, male flower zone: About 3.5 cm. Length, sterile zone: About 2.5 cm. Length, female flower zone: About 1.5 cm. Diameter, male flower zone: About 8 mm. Diameter, sterile flower zone: About 5 mm. Diameter, female flower zone: About 9 mm. Shape: Columnar. Apex: Acute. Base: Obtuse. Aspect: Upright. Color, mature, male zone: Close to 11D. Color, mature, sterile zone: Close to 11D. Color, mature, female zone: Close to 8C, 8D and 155B. Male flowers: Quantity per spadix: About 110. Shape: Obovate. Height: About 2.5 mm. Diameter: About 3 mm. Pollen amount: Moderate. Pollen color: Close to 9D. Female flowers: Quantity per spadix: About 105. Shape: Obovate. Height: About 2.5 mm. Diameter: About 1 mm to 1.2 mm. Stigma color: Close to 8C and 8D. Ovary color: Close to 155B.

*Scape*.—Length: About 21.2 cm. Diameter: About 5 mm. Strength: Sturdy; flexible. Aspect: Mostly erect. Texture: Smooth, glabrous; glaucous. Color, just below spathe: Close to 147C stippled and streaked with close to 200C to 200D. Color, overall: Close to 199D tinged with close to 182D and 147C, stippled, streaked and striped with close to 200C.

*Seeds and fruits*.—To date, seed and fruit development have not been observed on plants of the new *Caladium*.

Disease & pest tolerance: Plants of the new *Caladium* have been observed to have above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Chinook' as illustrated and described.

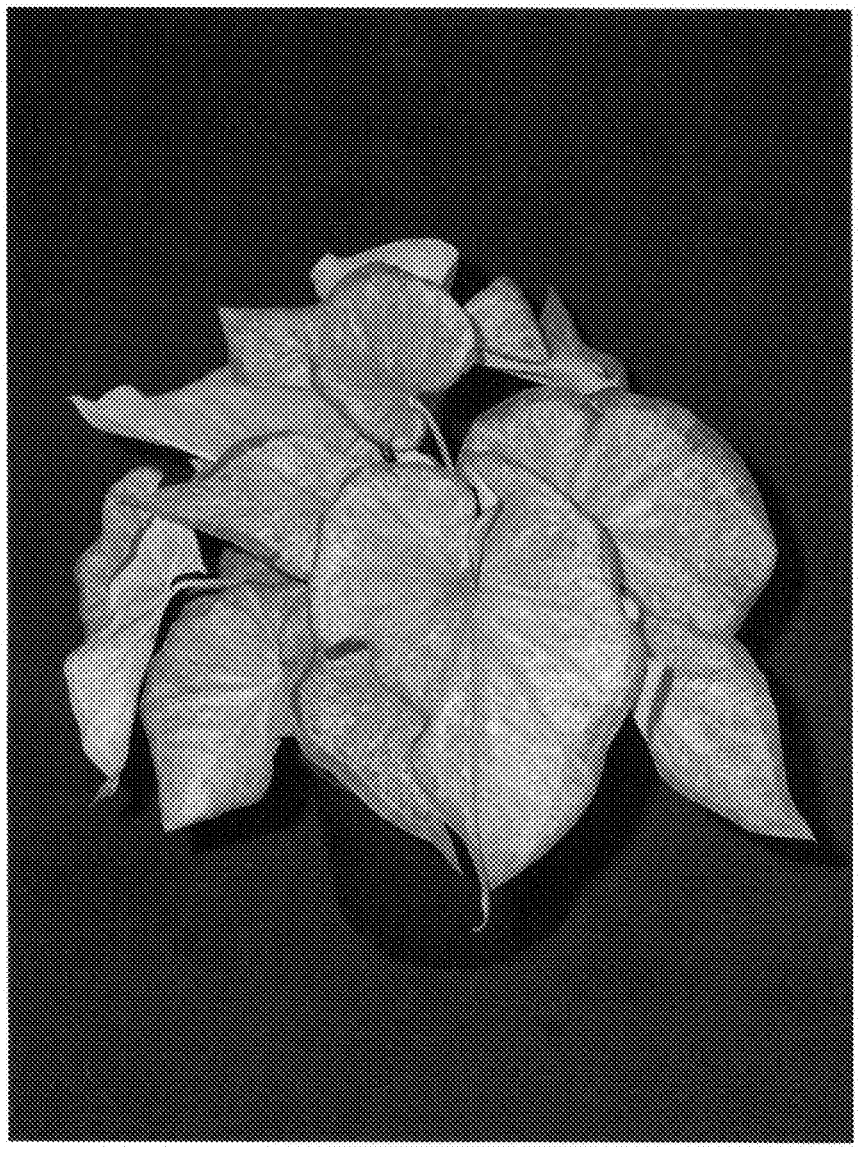

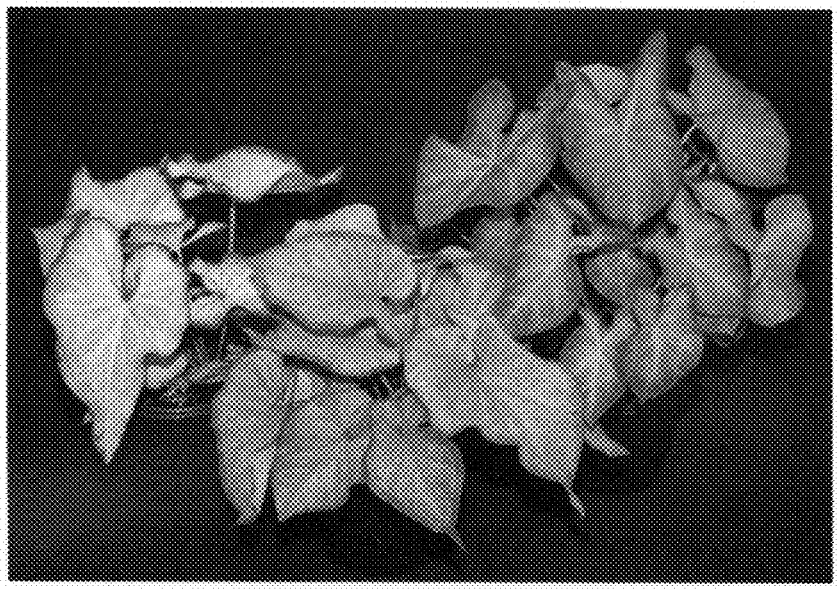
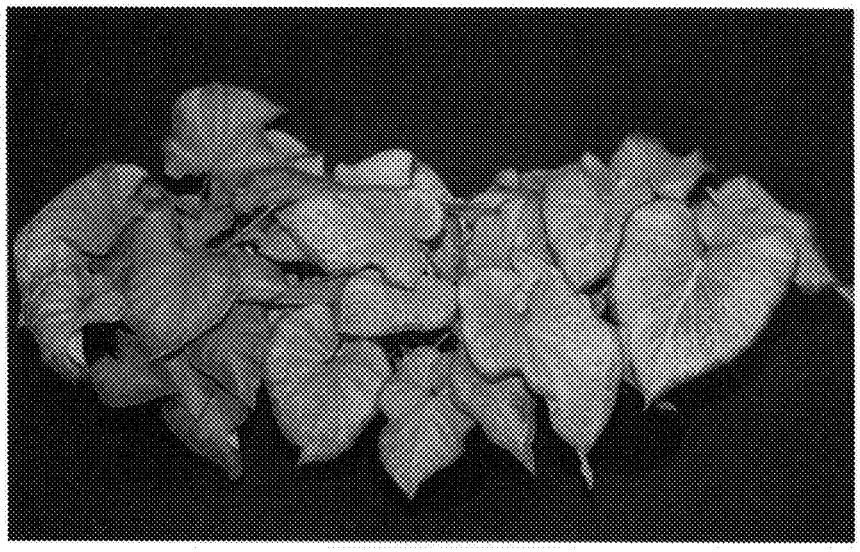

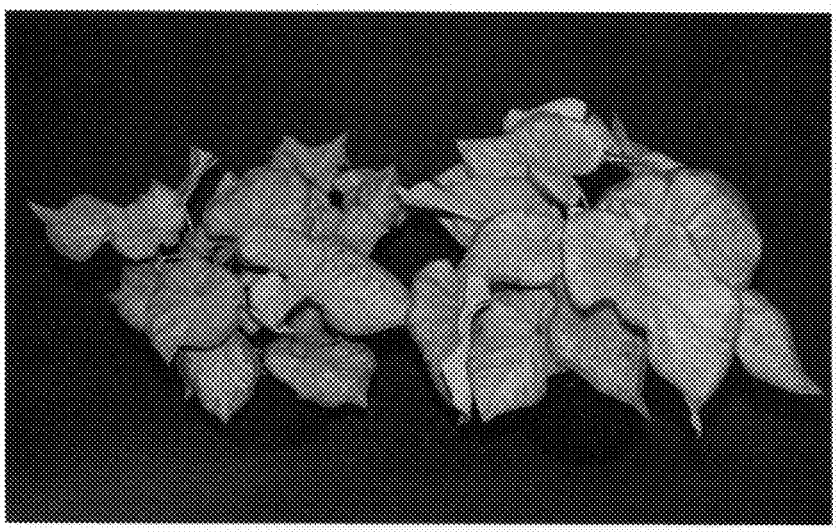
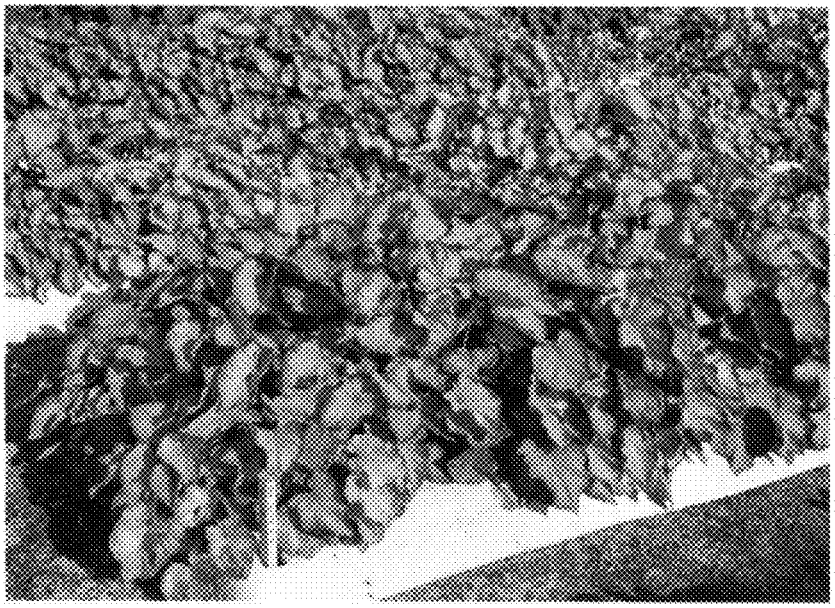

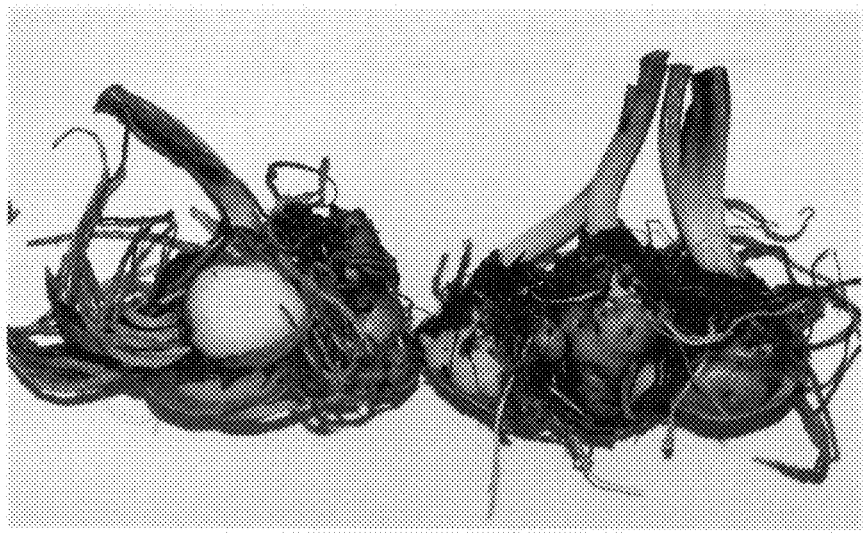
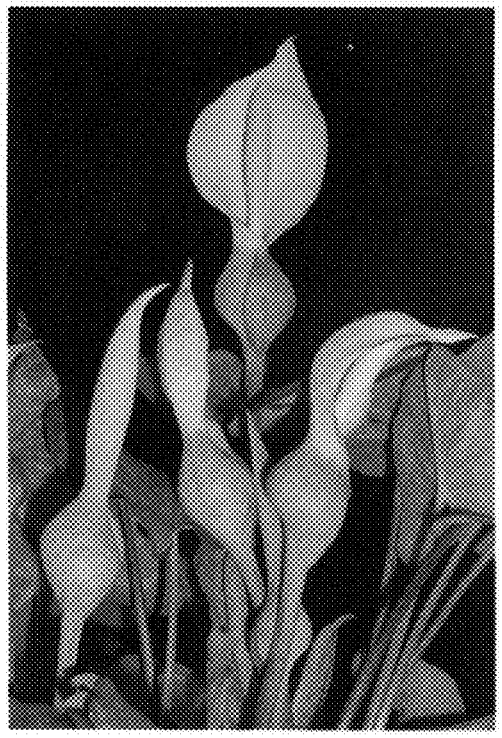

* * * * *